United States Patent [19]
Nishino et al.

[11] Patent Number: 6,071,968
[45] Date of Patent: Jun. 6, 2000

[54] PHENYLENEDIAMINE DERIVATIVE RADICAL SCAVENGER, BRAIN-INFARCTION DEPRESSANT, AND BRAIN-EDEMA DEPRESSANT

[75] Inventors: Chikao Nishino; Kentaro Adachi; Kazayuki Miyazawa, all of Kanagawa; Ryuhei Inada; Tatsuya Otake, both of Tokyo, all of Japan

[73] Assignee: Shiseido Co., Ltd., Tokyo, Japan

[21] Appl. No.: 09/097,414

[22] Filed: Jun. 16, 1998

[51] Int. Cl.[7] ................................................. A01N 37/18
[52] U.S. Cl. ................................................................ 514/617
[58] Field of Search .............................................. 514/617

[56] References Cited

FOREIGN PATENT DOCUMENTS

| 474403 A1 | 3/1992 | European Pat. Off. . |
| 3830054 A1 | 3/1990 | Germany . |
| 6-116143 | 4/1994 | Japan . |

OTHER PUBLICATIONS

Passage from EP 474,403 A1 of Background Section on p. 2, lines 43–45, of CA: 74:96312e of 1971.
Shiseido Co Ltd., Abstract, Jap. Patent Application 07344947, Jun. 17, 1997.
Abstract of Nishino et al., of Jp 09143136 A2, Jun. 3, 1997.
Klosa, J. Praket. Chem. 19(4), 45–55(1963) (With Chemical Abstract 11349), German language.
Gupta,, Gupta, Search for New Local Anaesthetics. Part IV, English Language, J. Indian Chem. Soc. 34.528–530(1957).
Hassner et al., Synthetic Methods. Part 23 Rearrangement of Some Hydroxamic Acids Into Amides. A Self–Condensation Leading to Disproportionation English Language, J. Chem. Soc. Perkin. Trans. 733–737(1988).

Shiseido Co., Ltd., Abstract, Jap. Patent Application 07344947, Jun. 17, 1997.

*Primary Examiner*—Dwayne C. Jones
*Attorney, Agent, or Firm*—Snider & Chao, LLP; Ronald R. Snider; Fei-Fei Chao

[57] ABSTRACT

A radical scavenger in accordance with the present invention comprises, as an effective ingredient, a phenylenediamine derivative or a pharmacologically acceptable salt thereof expressed by the following formula 1:

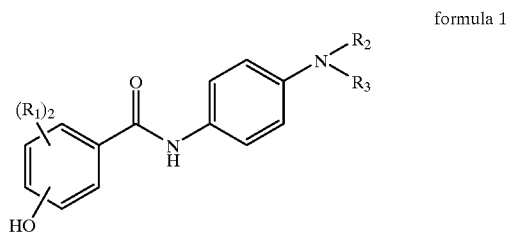

formula 1 wherein $R_1$ represents a lower alkyl group; and each of $R_2$ and $R_3$ represents a hydrogen atom, an alkyl group having 1–10 carbon atoms, an alkenyl group having 1–10 carbon atoms, or benzyl group.

The phenylenediamine derivative above mentioned, as a radical scavenger, has a lipid peroxidation inhibitory activity so as to be available for inhibiting brain infarction or brain edema.

11 Claims, 1 Drawing Sheet

REACTION FORMULA A

REACTION FORMULA B

REACTION FORMULA C

PHENYLENEDIAMINE DERIVATIVE RADICAL SCAVENGER, BRAIN-INFARCTION DEPRESSANT, AND BRAIN-EDEMA DEPRESSANT

RELATED APPLICATIONS

This application is incorporating by reference Japanese Patent Application No. 7-344947 filed on Dec. 5, 1995, which has the laid open publication (JP09-157236) date of Jun. 17, 1997.

FIELD OF THE INVENTION

The present invention relates to a phenylenediamine derivative and, in particular, to a derivative effective as a radical scavenger in organisms.

BACKGROUND OF THE INVENTION

In recent years, attention has been paid to influences of active oxygen and free radical upon organisms. Active oxygen and free radical are always generated and eliminated within an organism as long as the organism continues to live while using oxygen. In general, they act advantageously to the organism as a part of organism protection. However, when they are generated in an amount exceeding the protecting ability of the organism against the radical, they may attack the components of the organism constituting membranes and tissues of thereof, thereby causing various pathologies and malignancies. At present, the pathologies and diseases which may be attributable to active oxygen and free radical are numerous and their examples include cerebral nerves diseases such as brain infarction, brain edema, and parkinsonism; lung diseases such as lung oxygen intoxication and adult respiratory distress syndrome; circulation system diseases such as ischemic heart diseases (e.g., myocardial infarction and arrhythmia), and arteriosclerosis; and digestive organs diseases such as peptic ulcer, ulcerative colitis, and Crohn's disease.

Under these circumstances, consequently, there have been attempts to apply scavengers of active oxygen and free radical to medicaments for the above-mentioned diseases. For example, with respect to brain edema, mannitol, which is a mild radical scavenger, has been clinically used, though it is necessary continuous administration for two weeks. Recently, radical scavengers such as AVS (currently being applied) and MCI186 (currently being clinically tested in the third phase) have been developed recently. The sole target disease of these compounds is, however, brain edema. There has been no medical drug in which a radical scavenger is used for suppressing brain infarction.

On the other hand, a recombinant of SOD has become available and has been administered to patients so as to study its tissue-protecting effect. Acute myocardial infarction is one of its target diseases. By contrast, no radical scavenger other than SOD has been known as a medicament for this disease. With respect to arrhythmia, on the other hand, only lidocaine, which is a local anesthetic, has been clinically used.

SUMMARY OF THE INVENTION

In view of the foregoing prior art, an object of the present invention is to provide a low-molecular compound which is, as a radical scavenger, effective against brain edema and brain infarction.

Another object of the present invention is to provide a low-molecular compound which is effective against various diseases which are attributable to active oxygen and free radical.

As a result of diligent studies of the inventors for attaining the above mentioned objects, it has been found that a specific phenylenediamine derivative and its pharmacologically acceptable salts are effective, as a radical scavenger, against brain edema and brain infarction, thereby accomplishing the present invention.

Namely, a radical scavenger in accordance with the present invention is characterized by comprising, as an effective ingredient, a phenylenediamine derivative or a pharmacologically acceptable salt thereof expressed by the following formula 1 together with a pharmaceutically acceptable carrier and/or adjuvant:

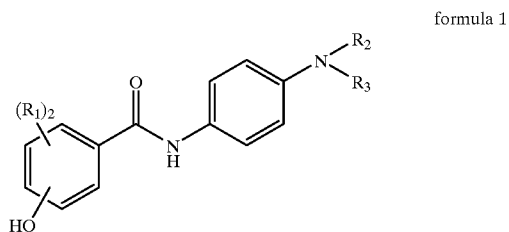

formula 1 wherein $R_1$ represents a lower alkyl group, and each of $R_2$ and $R_3$ represents a hydrogen atom, an alkyl group having 1–10 carbon atoms, an alkenyl group having 1–10 carbon atoms, or benzyl group.

A brain infarction depressant in accordance with the present invention is characterized by comprising said radical scavenger.

A brain edema depressant in accordance with the present invention is characterized by comprising said radical scavenger.

A method for inhibiting a brain infarction in man or mammals in accordance with the present invention is characterized by administering an effective amount of said radical scavenger to a host.

A method for inhibiting a brain edema in man or mammals in accordance with the present invention is characterized by administering an effective amount of said radical scavenger to a host.

DETAILED DESCRIPTION OF THE INVENTION

Figure 1:
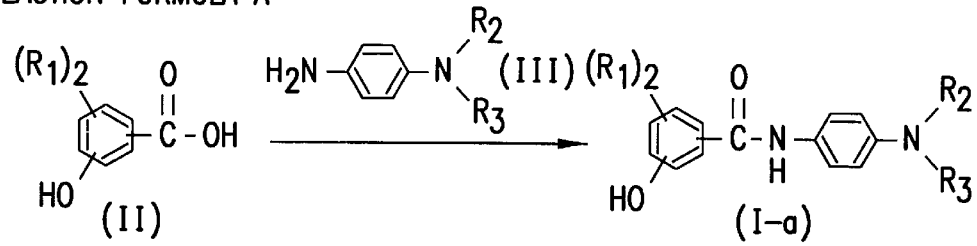
FIGS. 1 and 2 show examples of steps for manufacturing the phenylenediamine derivative in accordance with the present invention.

In the present invention, a lower alkyl group found at $R_1$ refers to a straight or branched alkyl group having 1 to 6 carbon atoms. Examples thereof include methyl, ethyl, n-propyl, n-butyl, isopropyl, isobutyl, 1-methylpropyl, tert-butyl, n-pentyl, 1-ethylpropyl, isoamyl, and n-hexyl groups. A Preferable example of $R_1$ is tert-butyl group.

$R_2$ and $R_3$, which may be identical to or different from each other, are hydrogen atoms, alkyl groups having 1–10 carbon atoms, alkenyl groups having 1–10 carbon atoms, or benzyl groups. The alkyl and alkenyl group at $R_2$ and $R_3$ may be a straight or branched group. In branched alkenyl group, while the double bond has two configurations, namely, cis and trans, each double bond may have either configuration. The benzyl group may be substituted by a substituent. When $R_2$ and $R_3$ are alkyl groups, methyl group is preferable therefor.

A preferable example of a radical scavenger in accordance with the present invention comprises a phenylenediamine derivative or a pharmacologically acceptable salt thereof which, in formula 1, $R_1$ represents a lower alkyl group; and each of $R_2$ and $R_3$ is an alkenyl group having 1–10 carbon atoms or benzyl group. More preferably, the phenylenediamine derivative or the pharmacologically acceptable salt thereof is expressed by the following formula 2:

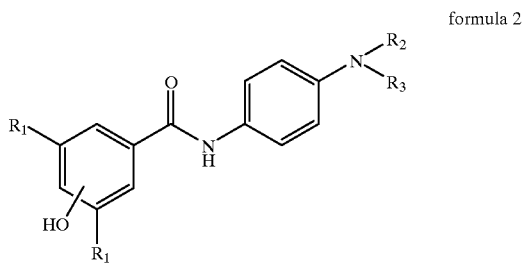

formula 2 wherein $R_1$ represents a lower alkyl group; and each of $R_2$ and $R_3$ represents an alkenyl group having 1–10 carbon atoms or benzyl group.

In formula 1 or 2, $R_1$ is preferably tert-butyl group.

Also, a preferable example of a radical scavenger in accordance with the present invention comprises a phenylenediamine derivative or a pharmacologically acceptable salt thereof expressed by the following formula 3:

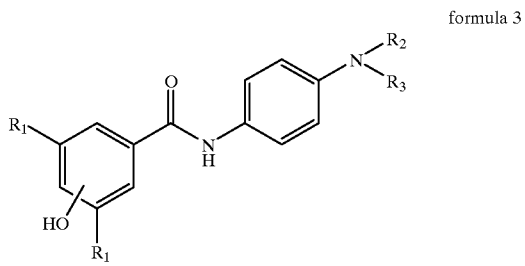

formula 3 wherein $R_1$ represents a lower alkyl group; and each of $R_2$ and $R_3$ represents an alkyl group having 1–10 carbon atoms.

In formula 3, $R_2$ and $R_3$ are preferably methyl groups.

Further, in formula 3, $R_1$ is preferably tert-butyl group.

Most of the phenylenediamine derivatives expressed by formula 1 are novel compounds which have not been conventionally disclosed. Also, the effect as a radical scavenger, brain-infarction inhibition effect, and brain-edema inhibition effect of the compounds expressed by formula 1 never have been known at all.

In Japanese Unexamined Patent Application No. 6-116143, a part of the compounds which are expressed by formula 3. However, it is only disclosed that the effects are a cholesterol-in-blood lowering effect and macrophage-foaming inhibition effect and that the uses are an anti-hyperlipemia drug and an antiarteriosclerosis drug. Also, the pharmacological effect in accordance with the present invention or a effect related thereto is not disclosed at all. Accordingly, the pharmacological effect of the present invention by the compounds expressed by formula 3 never has been known and it has been definite by the present invention for the first time. The present invention includes a radical scavenger, brain infarction depressant, and brain edema depressant comprising, as an effective ingredient, the compounds or a pharmacologically acceptable salt thereof expressed by formula 3.

Also, as similar compounds of a phenytenediamine derivative in accordance with the present invention, there have been known a phenylenediamine derivative having anti-thrombocyte aggregation effect in DE 3,830,054, a phenylenediamine derivative having anti-hypnotic effect and sedative effect anti-tumor effect in U.S. Pat. No. 2,870, 146, a phenylenediamine derivative in J. Prakt. Chem. 19(4), 45(1963), and a phenylenediamine derivative having local anesthesia effect in J. Indian. Chem. Soc. 34, 528(1957). However, these have no relation to the pharmacological effect of the present invention. Further, the derivative of the present invention is characterized in that has two of $R_1$ and a hydroxyl group on benzene ring as shown in the above-mentioned formula 1. Such compound was not shown in the above.

The phenylenediamine derivative and its pharmacologically acceptable salts expressed by formula 1 that are preferable as a main ingredient of the radical scavenger, brain-infarction depressant, and brain-edema depressant in accordance with the present invention, as a radical scavenger, have antioxidant effect and lipid peroxidation suppressing effect as well as a high safety. Accordingly, they are effective as medicaments for preventing and curing various damages attributable to radicals generated by ischemic reperfision or the like such as brain infarction and brain edema. Also, they are expected to be effective against the other ischemic reperfusion damages. Further, unlike the conventional radical scavengers, some kinds of the compound of the present invention has effective, by one drug, against both brain edema and brain infarction.

Figure 2:
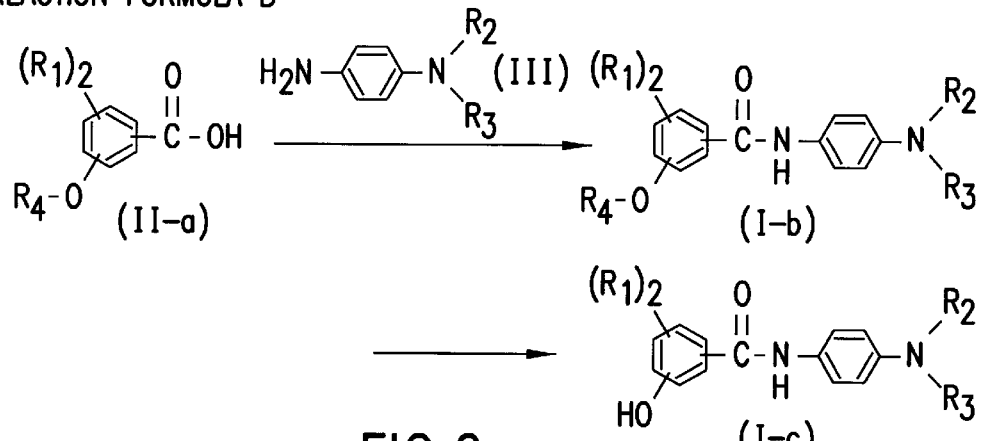

The compound (I) expressed by formula 1 can be made by reaction formula A or B shown in FIG. 1 or 2. As its manufacturing method, a general method disclosed in "New Experimental Chemistry Course" (Maruzen Co.) or "Peptide Synthesis" (Maruzen Co.), for example, can be used.

First, in reaction formula A shown in FIG. 1, $R_1$, $R_2$, and $R_3$ are defined as those in formula (I).

In reaction formula A, from the carboxylic acid (II) and the amine (III), the amide (I-a) in accordance with the present invention can be obtained. In this reaction, known amide-bond forming reactions such as a method proceeding by way of a mixed anhydride, a method proceeding by way of an acid chloride, a method using a condensing agent, a method using a carbonyldiimidazole, and a method using with an azide can be used.

In the mixed anhydride method, an activator such as diphenylphosphinic chloride, phosphorus oxychloride, ethyl chloroformate, isobutyl chloroformate, or pivaloyl chloride is used to convert the carboxylic acid (II) into its corresponding acid anhydride and then the latter is reacted with the amine (III). As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of −15° C. to the reflux temperature of the solvent.

In the acid chloride method, for example, phosphorus pentachloride, phosphorus trichloride, or thionyl chloride is used to convert the carboxylic acid (II) into its corresponding acid chloride and then the latter is reacted with the amine (III). As an additive, for example, an organic base such as triethylamine, pyridine, or N-methylmorpholine, an inorganic base such as sodium hydroxide; or a salt such as sodium acetate or potassium carbonate can be used. As a solvent, for example, a halogenated hydrocarbon such as dichloromethane or chloroform, an aromatic compound such as benzene, toluene, xylene, or pyridine; an ether such as diethyl ether, tetrahydrofuran, or dioxane, an amide such as dimethylformamide or dimethylacetamide; dimethylsulfoxide; water; or the mixture thereof can be used. While the reaction temperature and reaction time may be changed according to the material compounds used, the reaction is usually effected at a temperature within the range of 0° C. to the reflux temperature of the solvent.

In the method using a condensing agent, for example, a carbodiimide such as N, N'-dicyclohexylcarbodiimide (DCC) or 1-ethyl-(3-dimethylaminopropyl)carbodiimide hydrochloride (WSCI) or a chloride such as titanium tetrachloride or silicon tetrachloride can be used. As a solvent, for example, a halogenated hydrocarbon such as dichloromethane or chloroform; an aromatic compound such as benzene, toluene, xylene, or pyridine; an ether such as tetrahydrofuran or dioxane, an amide such as dimethylformamide or dimethylacetamide; or dimethylsulfoxide can be used. If necessary, this reaction may be effected while l-hydroxy benzotriazole (HOBt) or N-hydroxysuccinimide (HOSu) is added thereto. While the reaction temperature and reaction time may be changed according to the material compounds used, the reaction is usually effected at a temperature within the range of −78° C. to the reflux temperature of the solvent.

In the method using carbonyl diimidazole (CDI), 1,1'-carbonyldiimidazole is used to convert the carboxylic acid (II) into its N-acyl derivative and then the latter is reacted with the amine (III). As a solvent, for example, a halogenated hydrocarbon such as dichloromethane or chloroform; an aromatic compound such as benzene, toluene, or xylene; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of 0° C. to the reflux temperature of the solvent.

In the azide method, an activator such as diphenylphosphorylazide is used to convert the carboxylic acid (II) into its corresponding azide and then the latter is reacted with the amine (III). As an additive, for example, an organic base such as triethylamine, pyridine, or N-methylmorpholine can be used. As a solvent, for example, a halogenated hydrocarbon such as dichloromethane or chloroform; an aromatic compound such as benzene, toluene, xylene, or pyridine; an ether such as tetrahydrofuran or dioxane; an amide such as dimethylformamide or dimethylacetamide; or dimethylsulfoxide can be used. While the reaction temperature and reaction time may be changed according to the material compounds used, the reaction is usually effected at a temperature within the range of 0° C. to the reflux temperature of the solvent.

In the ester-bond formation by the dehydrating condensation, for example, methods using, as a catalyst, a mineral acid such as sulfuric acid or hydrochloric acid, an organic acid such as p-toluene sulfonic acid, or a Lewis acid such as boron trifluoride etherate or methods using a coexisting desiccating agent such as magnesium sulfate anhydride or molecular sieve can be used. Also, a condensing agent such as trifluoroacetic anhydride or N,N'-dicyclohexylcarbodiimide (DCC) can be used. In this case, pyridine, 4-dimethylaminopyridine, or the like can be used therewith. Further, in the presence of triphenylphosphine, diethyl diazocarboxylate can be used. As a solvent, for example, a halogenated hydrocarbon such as dichloromethane or chloroform; an aromatic compound such as benzene, toluene, xylene, or pyridine, an ether such as tetrahydrofuran or dioxane; or an amide such as N,N-dimethylformamide or N,N-dimethylacetamide can be used. While the reaction temperature and reaction time can be changed according to the material compounds used, the reaction is usually effected at a temperature within the range of 0° C. to the reflux temperature of the solvent.

Specifically, for example, in the method using the condensing agent, the carboxylic acid (II) is dissolved in dichloromethane, N,N-dimethylformamide, or the like and, after a condensing agent such as DCC or WSCI is added thereto, in or without the presence of HOBt or HOSu as an additive, and the resulting mixture is stirred, the amine (III) is added thereto and the reaction is effected at a temperature within the range of 0° C. to room temperature, - thereby attaining the aimed object.

In the mixed acid anhydride method, the reaction is effected at a temperature within the range of 0° C. to room temperature in the solvent such as chloroform by using diphenylphosphinic chloride as an activating agent and triethylamine as an additive, thereby attaining the aimed object.

Also, the compound in accordance with the present invention can be obtained by reaction formula B shown in FIG. 2. In reaction formula B, $R_1$, $R_2$, and $R_3$ are defined as those of formula (I). Also, $R_4$ represents a protective group of phenolic hydroxyl group and can use benzyl group, various substituted benzyl groups, benzyloxycarbonyl group, or tert-butyloxycarbonyl group, as long as no problem has occurred in the subsequent reaction.

At the first step in reaction formula B, the compound (I-b) can be obtained from carboxylic acid (II-a) and amine (III) by using a condensation method described in formula A. At the second step in reaction formula B, the compound (I-c) can be obtained by putting the compound (I-b) into deprotection.

The deprotection can use various known methods according to the types of protective group $R_4$. For example, a reductive removal method or a method by treating with acid can be used in the case where $R_4$ is benzyl group. Specifically, for example, palladium-carbon is used as catalyst under the catalytic reduction condition and the reaction is effected in the solvent such as ethanol at a temperature within the range of room temperature to the reflux temperature of the solvent, thereby attaining the aimed object.

Figure 3:
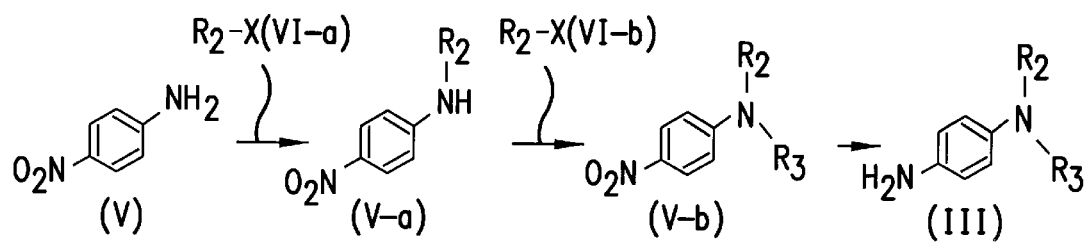
FIG. 3 shows an example of step for manufacturing material compound for synthesizing the phenylenediamine derivative in accordance with the present invention.

The material compound (II), (II-a), and (III) used in the above mentioned reaction formulas are commercially available or can be easily synthesized by known methods. For example, the material compound (III) can be synthesized as like reaction formula C shown in FIG. 3. In reaction formula C, $R_2$ and $R_3$ are defined as those in formula (I).

In reaction formula C, the objective compound (III) can be obtained by successively alkylating the compound (V) and by further reducing the nitro group.

In the alkylation at the first and second steps of the present reaction, the compound (V) is reacted with halide (VI-a) and (VI-b) so as to obtain the compound (V-b). This reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol, an aromatic compounds such as benzene, toluene, xylene, or pyridine; an ether such as diethyl ether, tetrahydrofuran, or dioxane; an amide such as N,N-dimethylformamide or N,N-dimethylacetamide; a sulfoxide such as dimethylsulfoxide; or a ketone such as acetone can be used. While the reaction temperature and reaction time may be changed according to the material compounds used, the reaction is usually effected at a temperature within the range of 0° C. to the reflux temperature of the solvent.

Reduction of the nitro group of the compound (V-b) at the third step in the reaction formula C can use the known reactions. For example, a condition such as Birch reduction, Benkesser reduction, or the reduction using metal hydride complex compound, and the like can be used.

In the case where Birch reduction is adopted, metal such as lithium, sodium, or potassium is used and liquid ammonia is used as a solvent and then the reaction is conducted by coexisting methanol, ethanol, t-butanol, or the like as a proton source. While the reaction temperature and reaction time may be changed according to the material compounds used, the reaction is usually effected at a temperature within the range of −78° C. to the reflux temperature of the solvent. In the case where Benkesser reduction is adopted, for example, methylamine, ethylamine, or ethylenediamine is used as a solvent and the reaction is effected at a temperature within the range of −78° C. to the reflux temperature of the solvent, thereby attaining the aimed object. In the case where the reaction using metal hydride complex compound is adopted, sodium boron hydroxide is used. Water, methanol, ethanol, isopropanol, or the like is used as a solvent and then the reaction is conducted in the presence of 10% palladium/carbon, cyano nickel complex ion, or dichlorobis (triphenylphosphine) nickel (II) as a catalyst. While the reaction temperature and reaction time may be changed according to the material compounds used, the reaction is usually effected at a temperature within the range of 0° C. to the reflux temperature of the solvent.

Specifically, for example, dichlorobis (triphenylphosphine) nickel (II) of catalyst is dissolved in ethanol and, after sodium boron hydroxide and the compound (V-b) are added thereto, the reaction is effected at a temperature within the range of 0° C. to the reflux temperature of the solvent, thereby attaining the aimed object.

The material compounds used in reaction formula C are commercially available or can be easily synthesized by known methods.

The compound expressed by formula (I) in accordance with the present invention can be changed to acid-added salts if necessary. Examples of the acid-added salts include salts in conjunction with inorganic acid such as hydrochloric acid, hydrobromic acid, sulfuric acid, or phosphoric acid and salts in conjunction with organic salts such as acetic acid, propionic acid, citric acid, lactic acid, oxalic acid, maleic acid, fumaric acid, succinic acid, tartaric acid, or methanesulfonic acid. These salts can be easily manufactured by normal methods.

When the phenylenediamine derivative in accordance with the present invention is used as a medicament for cerebral nerve diseases such as brain infarction and brain edema, it is generally used as a medicine for internal use or an injection.

When the compound of the present invention is used as a medicine for internal use, it may be administered orally as tablet, powder, granule, capsule, syrup, or the like as well as parenterally as suppository or the like. While the amount of administration may be outside of the range mentioned below according to the degree of symptom, personal difference, age, kind of symptom, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like. -

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxy propyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, bofneol, and cinnamon powder. If necessary, these tablet and granule can be coated with sugar-coating, gelatin-coating, and the like.

When the compound of the present invention is used as an injection, while the amount of administration may differ according to the degree of symptom, personal difference, age, or the like, usually 0 05 to 10 mg/kg or, preferably, 0.1 to 3 mg/kg is administered per day for an adult in a single dose or several doses.

The injection may be a sterile aqueous or non-aqueous solution, suspension, and emulsion. In such an injection, at least one active material is used as being mixed with at least one inactive aqueous diluent or inactive non-aqueous diluent. Further, if necessary, it may contain such adjuvants as antiseptic, wetting agent, emulsifier, dispersant, stabilizer, and dissolution adjuvant. In general, these are sterilized by filtration (e.g., by bacteria-blocking filter), compounding of sterilizer, or gamma-ray radiation or, after these treatments, turned into a solid composition by means of freeze-drying technique or the like and then sterile water or sterile injection diluent is added thereto immediately before use.

EXAMPLES

In the following, the embodiment of the present invention will be explained in further detail by using phenylenediamine derivatives in accordance with the present invention as examples.

Before the explanation of specific examples, the method for testing effects will be explained.

Lipid Peroxidation Inhibition Test i) Meaning

As a role of a radical scavenger in organismis, a lipid peroxidation inhibiroty activity by eliminating a free radical has been known. Therefore, in an automatic oxidation system using a rat brain homogenate, whether a sample compound having a radical-eliminating effect can actually have a lipid peroxidation inhibitory activity or not is investigated and its effectiveness is comparatively studied.

ii) Method

With reference to method of Shimamoto et. al. (Clinical Study of Free Radical, vol. 1, pp. 91–95, 1987), the following method was used. An SD-line male rat (7-week-old) was bled to death with a physiological saline perfusion under pentobarbital anesthesia. Then, its hemisphaerium cerebri was taken out and, while being cooled with ice, a 19-fold amount of 20 mM phosphoric acid buffer (pH 7.4) was added thereto. The resulting mixture was homogenized. To this mixture, 1 $\mu$M of the sample compound was added. After the resulting mixture was incubated for 1 hour at 37° C., the amount of generated lipid peroxide was determined by TBA method. Namely, to 0.2 ml of the homogenate, 0.2mM of 8.1% SDS, 1.5 ml of 20% acetic acid buffer (pH 3.5), and 1.5 ml of 0.8% TBA reagent were added. The resulting mixture was incubated for 1 hour at 95° C. and then rapidly cooled with ice. Subsequently, 1 ml of distilled water and 5 ml of n-butanol/pyridine mixed solution (15:1, v/v) were added thereto and the mixture was stirred. After the mixture was centrifuged, the butanol layer was collected therefrom and its absorbance (a) at 535 nm was measured as compared with a blank. Also, as a reference liquid, a 10 $\mu$M solution of 1,1,3,3-tetraethoxypropane (TEP) was added in place of the brain homogenate and its absorbance (A) was measured in a similar manner. In the blank, a phosphoric acid buffer was used in place of the brain homogenate. The peroxide concentration was calculated by the following equation and defined as the brain lipid peroxide amount:

peroxide concentration (nmol/g wet weight)=a/A×100

The sample compound was used as being dissolved in dimethylsulfoxide (DMSO). While the final concentration of DMSO was 2%, no influence upon the present system was observed.

iii) Judgment Standard

The lipid peroxidation inhibitory rate of the sample compound at the concentration of 1 $\mu$M was calculated from the amount of increase in lipid peroxide in solvent-added group (M) and that in sample compound added group (m):

lipid peroxidation inhibitory rate (%)={1−(m/M)}×100

Brain Infarction Inhibition Test i) Meaning

The brain infarction inhibitory activity in vivo is studied. According to this test, it can be judged whether the peripherally administered sample compound can pass through the blood-brain barrier or not.

ii) Method

For the experiment, 9 to 10-week-old Crj:Fischer-344 line male rats were used. Each of all the soluble sample compounds was dissolved in a physiological saline and then administered intravenously or intraperitoneally. Each of insoluble ones was suspended in a physiological saline containing 0.1% Tween 80 and administered intraperitoneally. Also, those dissolved in a physiological saline containing 0.5% Tween 80 were used for intravenous administration. The intraperitoneal administration was effected 20 minutes before reperfusion, whereas the intravenous administration was effected simultaneously with reperfision. As a control, only the base was administered. The surgical operation was effected in a manner similar to method of Koizumi et al. (Japanese Journal of Stroke, vol. 8, pp. 1–8, 1986) so as to form a middle cerebral artery (MCA) infarction model. Namely, the rat was subjected to inhalation anesthesia with 4% halothane and then, while the anesthesia was maintained with 1% halothane, fixed on face-up position. The neck portion was subjected to median incision such that the common carotid artery and outer carotid artery around the right carotid artery branching portion were separated from their surrounding connecting tissues and then ligated with a silk string. Further, the inner carotid artery starting portion was surrounded by a silk string so as to be ready for ligation and fixation which would be effected after insertion of an embolus. Then, the common carotid artery was incised and, from there, an embolus having a length of about 16 mm, in which a 4-0 surgical nylon string had been coated with a dental impression material, was inserted toward the inner carotid artery and its end near the nylon string was ligated and fixed to the inner carotid artery with the above mentioned silk string. Also, during the surgical operation, the body temperature was maintained by a small animal body temperature control apparatus in order to prevent it from lowering upon the whole anesthesia processes.

According to the foregoing operation, brain ischemia was effected for 2 hours and then the embolus was pulled out so as to effect reperfilsion. The brain was taken out two hours after the reperfusion and then 4 pieces of crown-like separated strips were prepared by 2-mm intervals from the lambda level toward the downstream. These strips were immersed in 2% triphenyltetrazorium chloride (TTC) solution and incubated at 37° C. for 10 minutes. Thus dyed brain strips were immersed in a phosphate-buffered 8% formalin solution for 1 to 2 days and then photographed under a stereo-microscope (SZH10 ORINPAS). Thereafter, for each crown-like strip, the area of infarction region was measured by Planimeter (PLANIX 5000 TAMAYA).

iii) Judgment Standard

The effects of the sample compound were represented by its individual inhibitory rate (%) which used the total area of the infarction regions, which had not been dyed with TTC in the 4 strips.

The significance test was effected by student t-test.

individual inhibitory rate(%)={1−(value in sample group/value in control group)}×100

Brain Edema Inhibition Test i)Meaning

The brain edema inhibitory activity in vivo is confirmed. According to this test, it can be judged whether the peripherally administered sample compound can pass through the blood-brain barrier or not.

ii) Method

By using a 7 to 9-week-old Fischer rat (Charles River Japan Inc.), an MCA infarction reperfusion model was formed according to method of Koizumi et al. (Japanese Journal of Stroke, vol. 8, pp. 1–8, 1986). Namely, the rat was fixed face-up position under anesthesia with 2% halothane and then its neck portion was subjected to median incision so as to separate the right common carotid artery therefrom to the carotid artery branching portion while carefully keeping the vagus nerve. The outer carotid artery and inner carotid artery around the carotid artery branching portion were separated from their surrounding connecting tissues. Then, the common carotid artery and outer carotid artery were ligated with a silk string. Further, the inner carotid artery starting portion was surrounded by a silk string so as to be ready for ligation and fixation which would be effected after insertion of an embolus string. Then, the common carotid artery was incised and, from there, an embolus string was inserted toward the inner carotid artery by about 15 to 16 mm and then ligated and fixed to the inner carotid artery with the above mentioned silk string. As a result of the foregoing operation, the tip of the embolus string proceeded beyond the MCA branching portion so as to enter the anterior cerebral artery by about 1 to 2 mm and formed infarction at the MCA inlet by the body portion of the embolus string. After the embolus string blocking the MCA starting portion was left for a predetermined time, it was pulled out under halothane anesthesia to effect reperfusion. Here, in this model, since the right common carotid artery has been ligated, the blood flow is supposed to be restarted from the left inner carotid artery and vertebral-basilar by way of the anterior and posterior communicating arteries. This experiment effected two-hour ischemia and two-hour reperfusion.

Here, the embolus string was prepared in the following manner. Namely, a tip of a 4-0 surgical nylon string having a total length of 16 mm was held over an alcohol lamp so as to form a ball with a diameter of 0.2 to 0.3 mm and then a length of about 5 mm on the nearer side therefrom was coated with a dental impression material with reference to the size of the ball, thereby forming the embolus string.

The brain moisture content was measured by wet and dry weight method. Namely, after the head of the animal which had been subjected to ischemia or ischemic reperfusion was severed and its brain was taken out. After the resection of the cerebellum, the fore-brain was separated into right and left hemispheres which were immediately weighed respectively as ischemia side and non-ischemia side, thereby yielding their wet weight. Further, after being dried at 110° C. for 24 hours, their weight was measured again to yield dry weight. From thus obtained wet weight and dry weight, the brain moisture content was determined by the following equation:

brain moisture content (%)={(wet weight−dry weight)/wet weight}×100

The sample compound was suspended in a 0.05% Tween 80/physiological saline and 5 ml/kg of the suspension was intraperitoneally administered 20 minutes before reperfusion. Also, to a control, the base was administered alone in a similar manner.

iii) Judgment Standard

The results obtained were expressed by mean value ±standard deviation. The significance test was effected by unpaired t-test or Welch's t-test and the difference was considered to be significant when the level of significance was less than 5% (P<0.05). The inhibitory rate was expressed by the following equation:

inhibitory rate(%)={(brain moisture content in control group−brain moisture content in sample group)/(brain moisture content in control group−brain moisture content in two-hour ischemia group)}×100

EXAMPLE 1

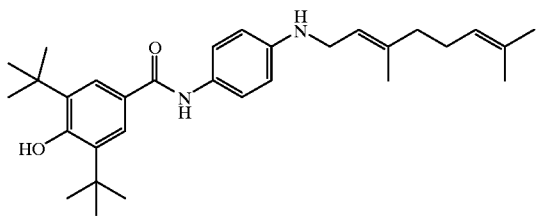

EXAMPLE 2

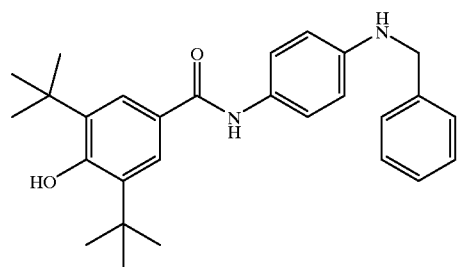

EXAMPLE 3

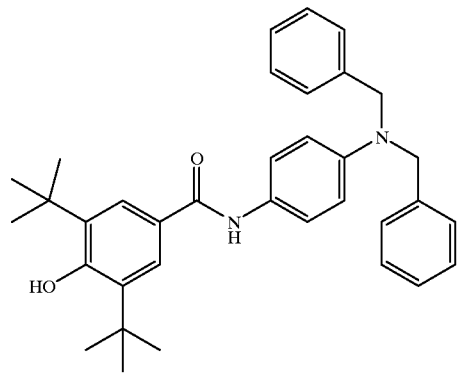

EXAMPLE 4

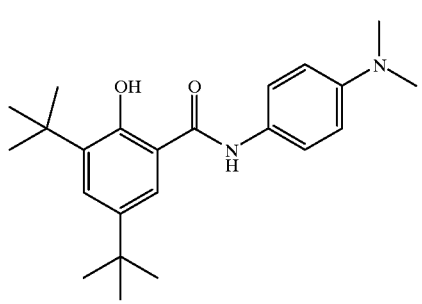

EXAMPLE 5

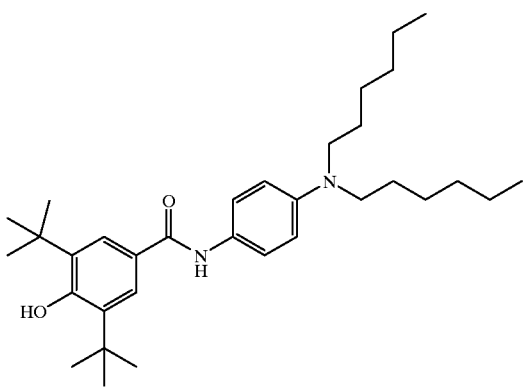

EXAMPLE 6

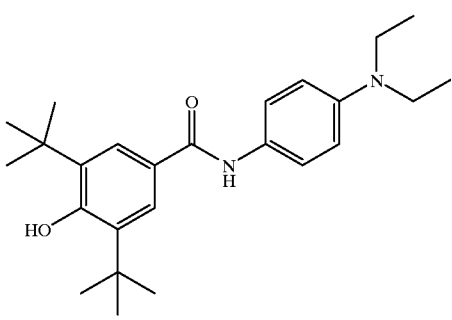

EXAMPLE 7

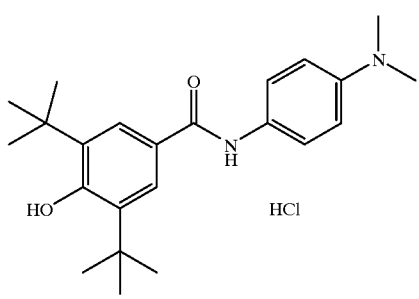

TABLE 1

| Sample compound | Lipid peroxidation inhibitory ratio | Brain infarction inhibitory ratio | Brain edema inhibitory ratio |
|---|---|---|---|
| Example 1 | 53.0% | 25.4%[1)] | |
| Example 2 | 64.6 | 2.5[1)] | |
| Example 3 | 21.4 | 32.9[2)] | |
| Example 4 | 28.6 | 31.2[2)] | 16.1[4)] |
| Example 5 | 37.2 | 13.8[1)] | 4.2[3)] |
| Example 6 | 19.7 | 6.8[2)] | |
| Example 7 | 41.1 | 21.0[2)] | 38.7[2)] |

[1)] dose was 50 mg/kg
[2)] dose was 100 mg/kg
[3)] dose was 30 mg/kg
[4)] dose was 10 mg/kg As can be seen from the foregoing TABLE 1, because the phenylenediamine derivatives and the salts thereof in accordance with the present invention had a high lipid peroxidation inhibitory activity, it is suggested that they are useful as a radical scavenger. Also, some compounds having brain infarction and brain edema inhibition activity were confirmed. It is extremely rare compound that is useful for brain infarction and brain edema by one drug as a radical scavenger like this.

In the following, synthetic methods of Examples 1 to 7 mentioned above will be shown.

EXAMPLE 1

4-nitroaniline (2.00 g), potassium carbonate (4.00 g), and geranyl bromide (3.24 g) were refluxed with stirring in acetone (70 ml) for 20 hours. The reaction mixture was filtrated under a vacuum and the filtrate was concentrated under a vacuum. The residue was purified by silica gel column chromatography (hexane:ethyl acetate=8:1). The obtained compound (0.52 g), sodium borohydride (0.21 g), and dichlorobis (triphenylphosphine) nickel (II) (0.25 g) were refluxed with stirring in ethanol-isopropanole mixed solution (40 ml) for an hour. The reaction mixture, with water added thereto, was extracted with ethyl acetate. The extract was washed with saturated sodium hydrogencarbonate aqueous solution and saturated brine successively, dried over sodium sulfate anhydride and then concentrated under a vacuum. The residue was dissolved in anhydrous methylene chloride (25 ml) and then 3,5-di-tert-butyl-4-hydroxybenzoic acid (0.47 g), triethylamine (2 ml), and 1-(3-dimethylaminopropyl)-3-ethylcarbodiimide hydrochloride (0.40 g) were added thereto. After being stirred for 18 hours at room temperature, the reaction mixture was washed with saturated sodium hydrogencarbonate aqueous solution and saturated brine successively, dried over sodium sulfate anhydride and then concentrated. The residue was purified by silica gel column chromatography (ethyl acetate:n-hexane=1:5), thereby yielding 0.35 g of the aimed compound, $^1$H-NMR (CDCl$_3$)δ 1.28(3H, s), 1.48(18H, s), 1.59(3H, s), 1.71(3H, s), 2.05(2H, m), 2.12(2H, m), 3.71(2H, d, J=6.4 Hz), 5.10(1H, m), 5.39(1H, m), 5.56(1H, s), 6.62(2H, d, J=8.8 Hz), 7.40(2H, d, J=8.8 Hz), 7.52(1H, m), 7.65(1H, m), 7.66(2H, s).

EXAMPLE 2

In a manner similar to Example 1, 4-nitroaniline (2.00 g) was subjected to benzylation with benzyl bromide (1.72 ml), reduction, and condensation with 3,5-di-tert-butyl-4-hydroxybenzoic acid (0.55 g) successively, thereby yielding 0.22 g of the aimed compound.

mp 176.2–178.0° C.

$^1$-NMR (DMSO-d$_6$) δ 1.41(18H, s), 4.25(2H, d, J=5.9 Hz), 6.07–6.10(1H, m ), 6.55(2H,d, J=8.8 Hz), 7.20–7.37 (8H, m), 7.61(2H, s), 9.65(1H, s).

EXAMPLE 3

In a manner similar to Example 1, 4-nitroaniline (2.00 g) was subjected to benzylation with benzyl bromide (4.95 g), reduction, and condensation with 3,5-di-tert-butyl-4-hydroxybenzoic acid (0.40 g) successively, thereby yielding 0.40 g of the aimed compound.

mp 207.8–209.0° C.

$^1$H-NMR (DMSO-d$_6$)δ 1.41(18H, s), 4.67(4H, s), 6.66 (2H, d, J=8.3 Hz), 7.23–7.37(13H, m), 7.60(2H, s), 9.69(1H, s).

EXAMPLE 4

3,5-di-tert-butyl-4-hydroxybenzoic acid (1.50 g) was dissolved in tetrahydrofuran (25 ml), and then t-hydroxybenzotriazole (1.06 g) and dicyclohexylcarbodiimide (1.28 g) were added thereto while being cooled with ice. After being stirred for 30 minutes, the reaction mixture, with N,N-dimethyl-1,4-phenylenediamine (0.82 g) added thereto, was stirred at room temperature for 15 hours. The reaction mixture was washed with saturated sodium hydrogencarbonate aqueous solution and saturated brine, dried over sodium sulfate anhydride and then concentrated under a vacuum. The residue was purified by silica gel column chromatography (n-hexane:ethyl acetate=5:1). The resulting solid was recrystallized from n-hexane/ethyl acetate, thereby yielding 1.20 g of the aimed compound.

mp 167.2–169.3° C.

$^1$H-NMR (CDCl$_3$) δ 1.34&1.43(each 9H, s), 2.96(6H, s), 6.75(2H, d, J=9.3 Hz), 7.28(1H, d, J=1.9 Hz), 7.37(2H, d, J=9.3 Hz), 7.49(1H, d, J=1.9 Hz), 7.74(1H, s).

EXAMPLE 5

In a manner similar to Example 1, 4-nitroaniline (2.00 g) was subjected to alkylation with n-hexyl iodide (6.14 g), reduction, and condensation with 3,5-di-tert-butyl-4-hydroxybenzoic acid (0.82 g) successively, thereby yielding 0. 19 g of the aimed compound.

mp 152.0–163.0° C.

$^1$H-NMR(CDCl$_3$)δ 0.90(6H, m), 1.31(12H, brs), 1.48 (18H, s), 1.56(2H, brs), 3.22–3.26(4H, m), 5.55(1H, s), 6.63(2H, d, J=8.8 Hz), 7.40(2H, m), 7.47(1H, s), 7.66(2H, s).

EXAMPLE 6

In a manner similar to Example 1, 4-nitroaniline (2.00 g) was subjected to alkylation with ethyl iodide (4.52 g), reduction, and condensation with 3,5-di-tert-butyl-4-hydroxybenzoic acid (1.29 g) successively, thereby yielding 0.89 g of the aimed compound.

mp 184.0–187.0° C.

$^1$H-NMR (CDCl$_3$) δ 1.15(6H, t, J=6.8 Hz), 1.48(18H, s), 3.34(4H, q, J=7.3 Hz), 5.56(1H, s), 6.69(2H, d, J=9.3 Hz), 7.42(2H, m), 7.49(1H, brs), 7.67(211, s).

EXAMPLE 7

3,5-di-tert-butyl-4-hydroxybenzoic acid (2.50 g) was dissolved in a mixture of dichloromethane (25 ml) and triethylamine (2.02 g), and then diphenylphosphinic chloride (2.06 g) was added thereto while being cooled with ice. After being stirred for 30 minutes, the reaction mixture, with N,N-dimethyl-1,4-phenylenediamine (1.36 g) added thereto, was stirred at room temperature for 15 hours. The reaction mixture was washed with saturated sodium hydrogencarbonate aqueous solution and saturated brine, dried over sodium sulfate anhydride and then concentrated under a vacuum.

The obtained solid was dissolved in diethyl ether and then IN hydrochloric acid was added thereto. After being stirred for 10 minutes at room temperature, the deposited crystals were collected by filtration, thereby yielding 1.06 g of the aimed compound.

mp 219.5° C.(dec.)

$^1$H-N(DMSO-d$_6$) δ 1.43(18H,s), 3.06(6H,s) 7.35–7.55 (1H,br), 7.68(2H,s) 7.70–7.85(1H,br), 10.1(1H,br).

What is claimed is:

1. A radical scavenger comprising, as an effective ingredient, a phenylenediamine derivative or a pharmacologically acceptable salt thereof expressed by the following formula I together with a pharmaceutically acceptable carrier and/or adjuvant:

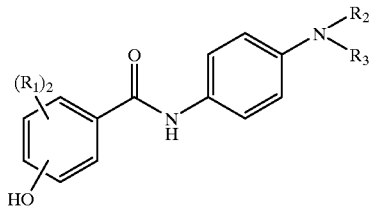

wherein R$_1$ represents a lower alkyl group; and each of R$_2$ and R$_3$ represents a hydrogen atom, an alkenyl group having 1–10 carbon atoms, or benzyl group, wherein at least one of R$_2$ and R$_3$ is an alkenyl group having 1–10 carbon atoms or benzyl group.

2. A radical scavenger according to claim 1, wherein R$_1$ is tert-butyl group.

3. A radical scavenger according to claim 1, wherein R$_1$ represents a lower alkyl group; and each of R$_2$ and R$_3$ represents an alkenyl group having 1–10 carbon atoms or benzyl group.

4. A radical scavenger according to claim 3, wherein the phenylenediamine derivative or the pharmacologically acceptable salt thereof is expressed by the following formula 2:

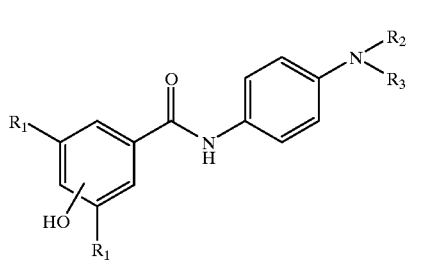

formula 2 wherein R$_1$ is a lower alkyl group; and each of R$_2$ and R$_3$ represents an alkenyl group having 1–10 carbon atoms or benzyl group.

5. A radical scavenger according to claim 4, wherein R$_1$ is tert-butyl group.

6. A method for inhibiting a brain infarction in man or mammals, which comprises administering an effective amount of a radical scavenger according to claim 1 to a host.

7. A method for inhibiting a brain edema in man or mammals, which comprises administering an effective amount of a radical scavenger according to claim 1 to a host.

8. A phenylenediamine derivative or a salt thereof expressed by the following formula 4:

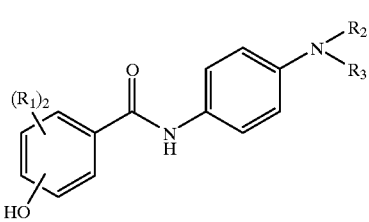

formula 4 wherein R$_1$ is a lower alkyl group; and each of R$_2$ and R$_3$ represents an alkenyl group having 1 10 carbon atoms or benzyl group.

9. A phenylenediamine derivative or a salt thereof according to claim 8, which is expressed by the following formula 5:

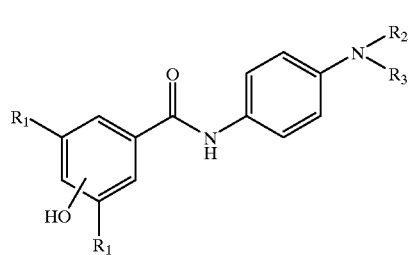

formula 5 wherein $R_1$ is a lower alkyl group, and each of $R_2$ and $R_3$ represents an alkenyl group having 1–10 carbon atoms or benzyl group.

10. A phenylenediamine derivative or a salt thereof according to claim 8, wherein $R_1$ is tert-butyl group.

11. A phenylenediamine derivative or a salt thereof expressed by the following formula of:

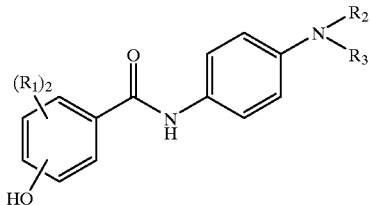

wherein $R_1$ is a lower alkyl group; $R_2$ is a hydrogen atom; and $R_3$ is an alkenyl group having 1–10 carbon atoms or benzyl group.

* * * * *